United States Patent [19]

Palmer

[11] Patent Number: 5,715,988
[45] Date of Patent: Feb. 10, 1998

[54] SURGICAL STAPLER WITH LOCKOUT MECHANISM

[75] Inventor: Mitchell J. Palmer, New Milford, Conn.

[73] Assignee: United States Surgical Corporation, Norwalk, Conn.

[21] Appl. No.: 514,638

[22] Filed: Aug. 14, 1995

[51] Int. Cl.⁶ .................................. A61B 17/072
[52] U.S. Cl. .................... 227/175.4; 227/175.3; 227/178.1; 227/180.1; 227/19
[58] Field of Search ............... 227/175.2, 175.3, 227/175.4, 176.1, 178.1, 180.1, 8, 19

[56] References Cited

U.S. PATENT DOCUMENTS

| | | |
|---|---|---|
| Re. 34,519 | 1/1994 | Fox et al. . |
| 2,174,219 | 9/1939 | Balma . |
| 2,246,647 | 6/1941 | Vancura et al. . |
| 3,079,606 | 3/1963 | Bobrov et al. . |
| 3,490,675 | 1/1970 | Green et al. . |
| 3,499,591 | 3/1970 | Green . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,304,236 | 12/1981 | Conta et al. . |
| 4,391,401 | 7/1983 | Moshofsky . |
| 4,429,695 | 2/1984 | Green . |
| 4,473,077 | 9/1984 | Noiles et al. . |
| 4,519,532 | 5/1985 | Foslien . |
| 4,520,817 | 6/1985 | Green . |
| 4,569,346 | 2/1986 | Poirier . |
| 4,576,165 | 3/1986 | Green et al. . |
| 4,576,167 | 3/1986 | Noiles . |
| 4,591,085 | 5/1986 | DiGiovanni . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,809,898 | 3/1989 | Gassner et al. . |
| 4,863,088 | 9/1989 | Redmond et al. . |
| 4,892,244 | 1/1990 | Fox et al. . |
| 4,955,959 | 9/1990 | Tompkins et al. . |
| 5,031,814 | 7/1991 | Tompkins et al. . |
| 5,083,695 | 1/1992 | Foslien et al. . |
| 5,141,144 | 8/1992 | Foslien et al. . |
| 5,156,315 | 10/1992 | Green et al. ............... 227/176.1 |
| 5,156,614 | 10/1992 | Green et al. . |
| 5,332,142 | 7/1994 | Robinson et al. ............ 227/175.2 |
| 5,366,133 | 11/1994 | Geiste . |
| 5,397,046 | 3/1995 | Savage et al. . |
| 5,413,267 | 5/1995 | Solyntjes et al. . |
| 5,415,335 | 5/1995 | Knodell, Jr. . |
| 5,445,304 | 8/1995 | Plyley et al. . |
| 5,458,279 | 10/1995 | Plyley . |
| 5,462,215 | 10/1995 | Viola et al. . |
| 5,465,896 | 11/1995 | Allen et al. . |
| 5,470,006 | 11/1995 | Rodak . |
| 5,470,008 | 11/1995 | Rodak . |
| 5,470,009 | 11/1995 | Rodak . |
| 5,472,132 | 12/1995 | Savage et al. . |

FOREIGN PATENT DOCUMENTS

| | | |
|---|---|---|
| 0156774 | 12/1986 | European Pat. Off. . |
| 0216532 | 4/1987 | European Pat. Off. . |
| 0399701 | 11/1990 | European Pat. Off. . |
| 0593920 | 4/1993 | European Pat. Off. . |
| 0539762 | 5/1993 | European Pat. Off. . |
| 0552050 | 7/1993 | European Pat. Off. . |
| 0598579 | 5/1994 | European Pat. Off. . |
| 0621006 | 10/1994 | European Pat. Off. . |
| 0365153 | 8/1995 | European Pat. Off. . |

*Primary Examiner*—Joseph J. Hall, III
*Assistant Examiner*—Jay A. Stelacone

[57] ABSTRACT

An apparatus for applying surgical fasteners is disclosed which includes a first lockout assembly configured to prevent premature ejection of fasteners during shipment and handling and a second lockout mechanism preventing reactuation of the apparatus after it has once been actuated. The second lockout mechanism includes a hook portion which engages a slot in the floor of the carrier channel.

21 Claims, 5 Drawing Sheets

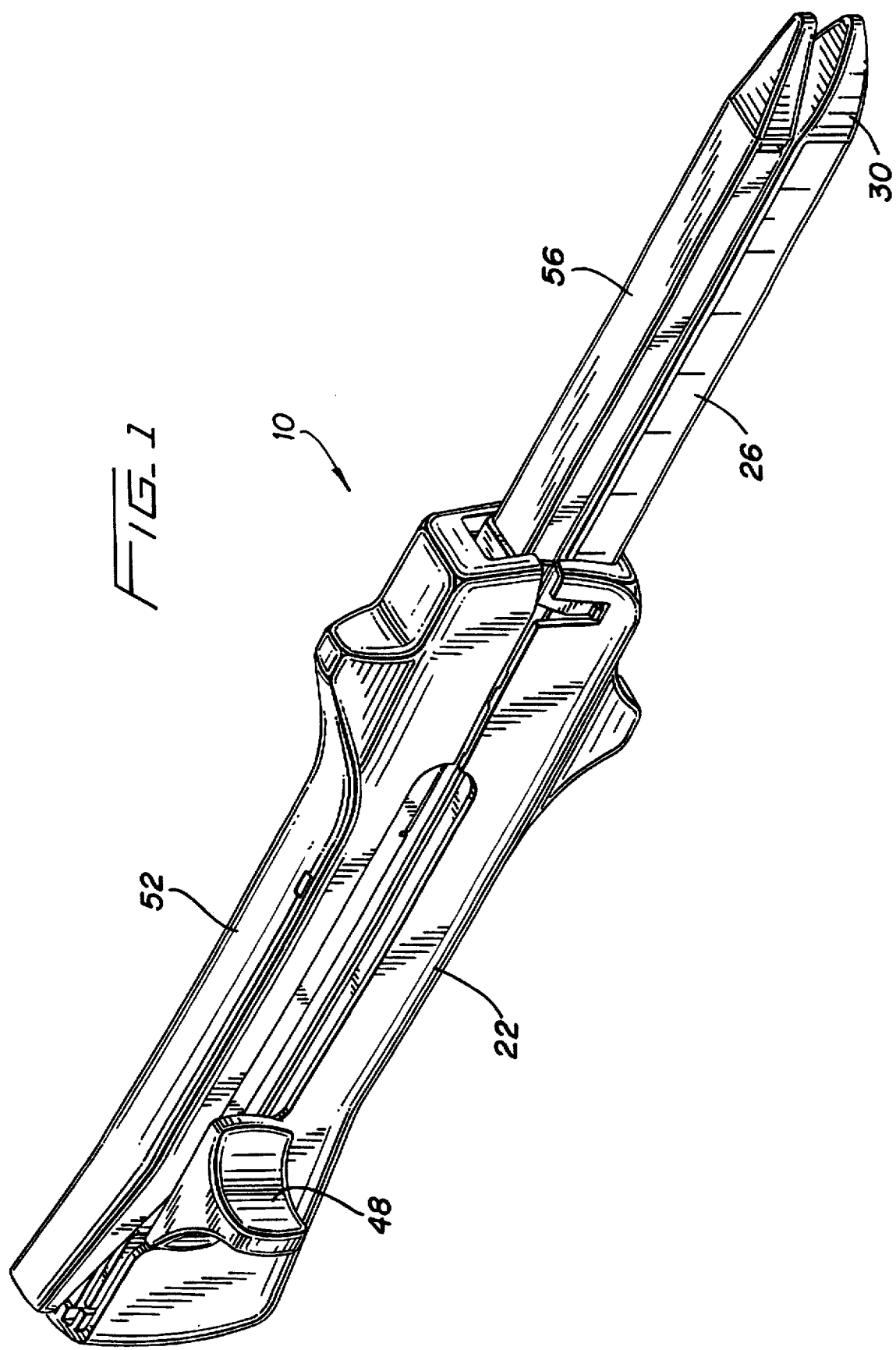

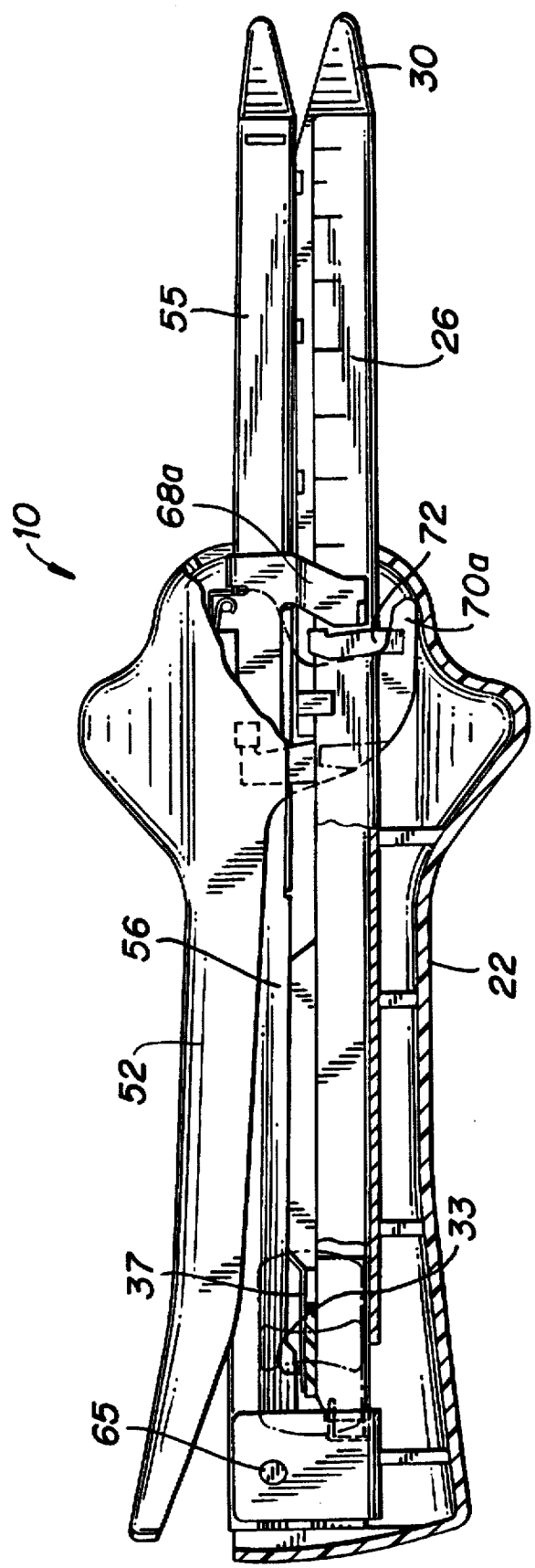

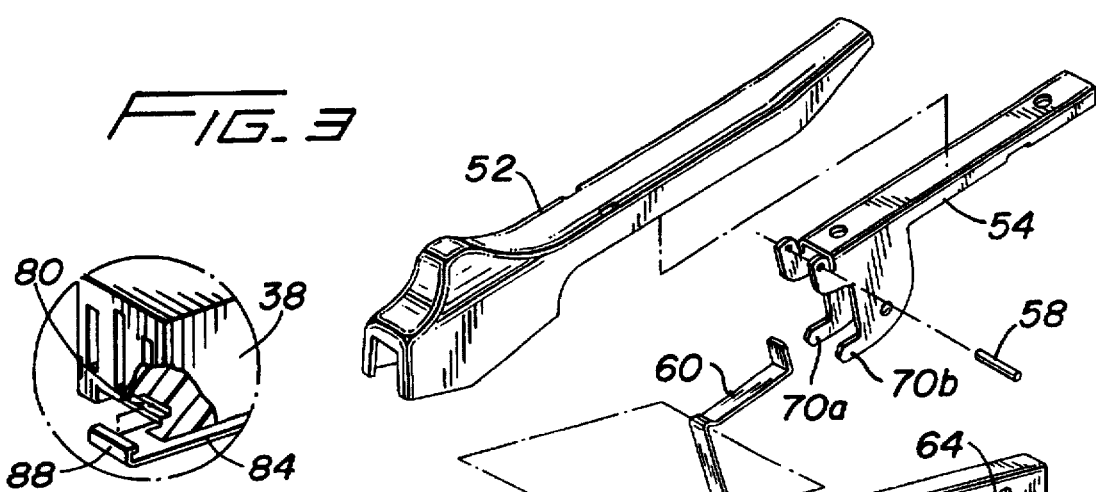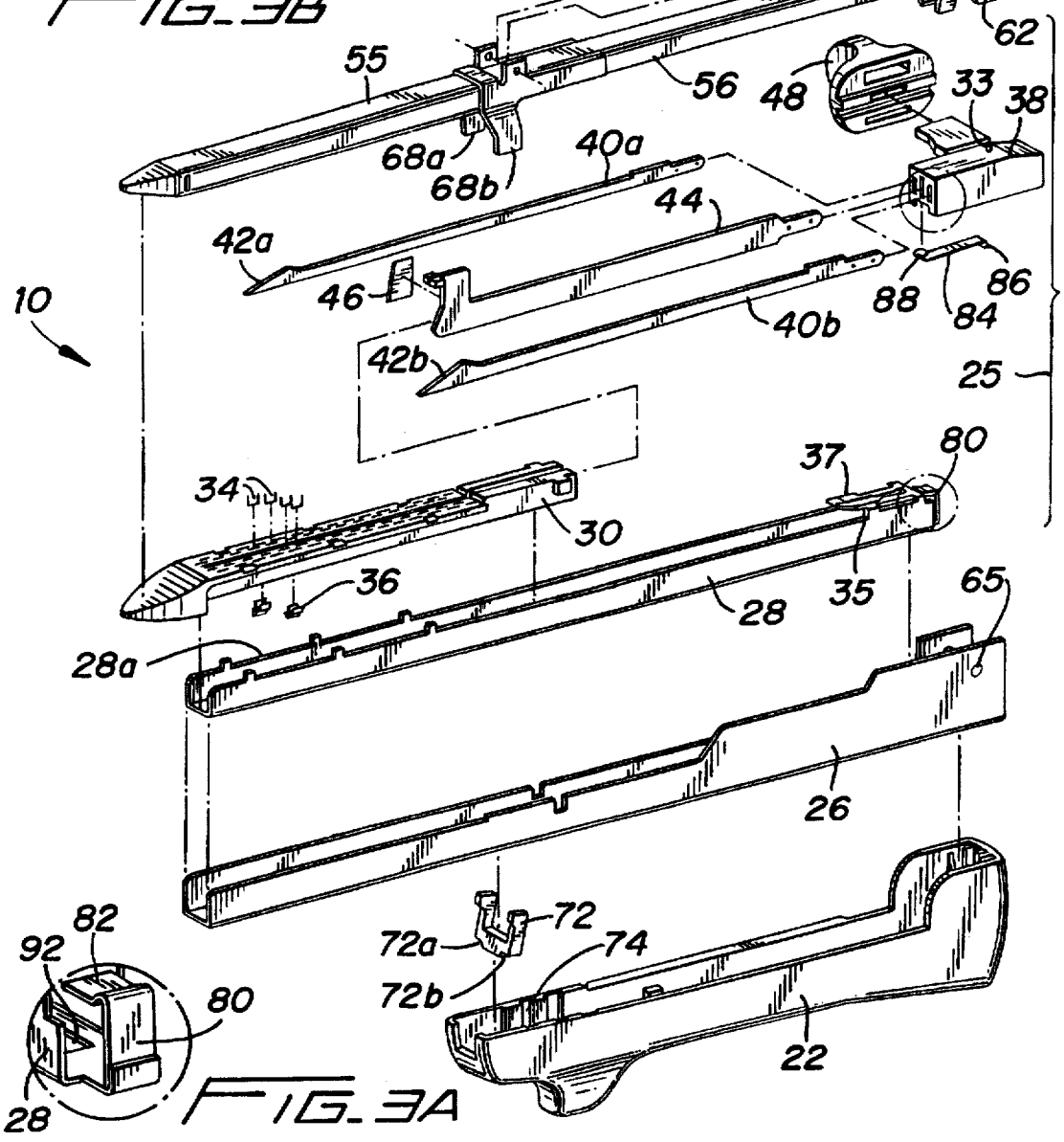

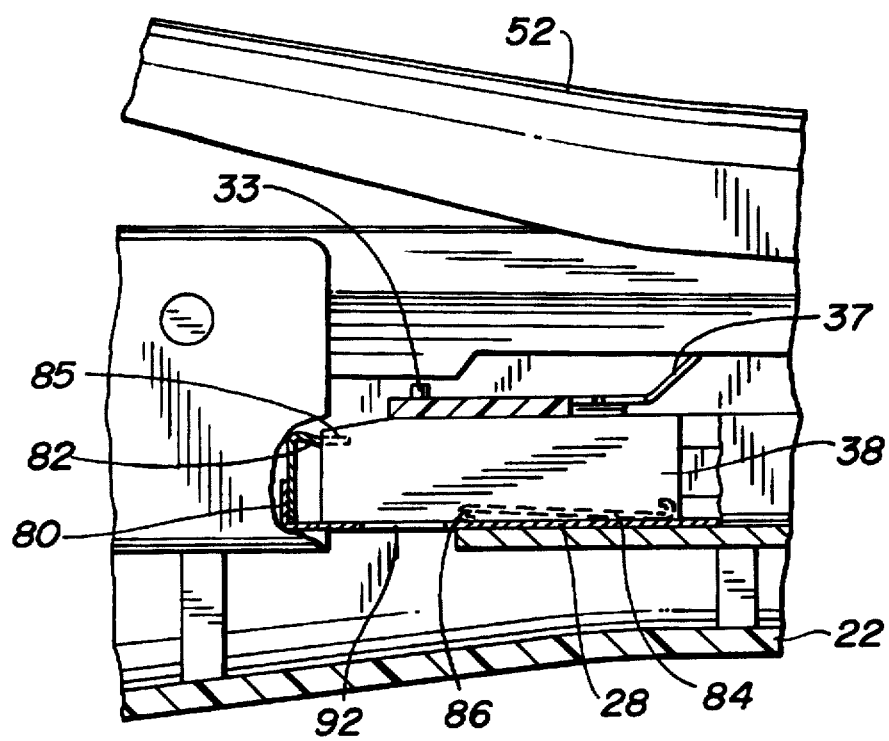
FIG_4
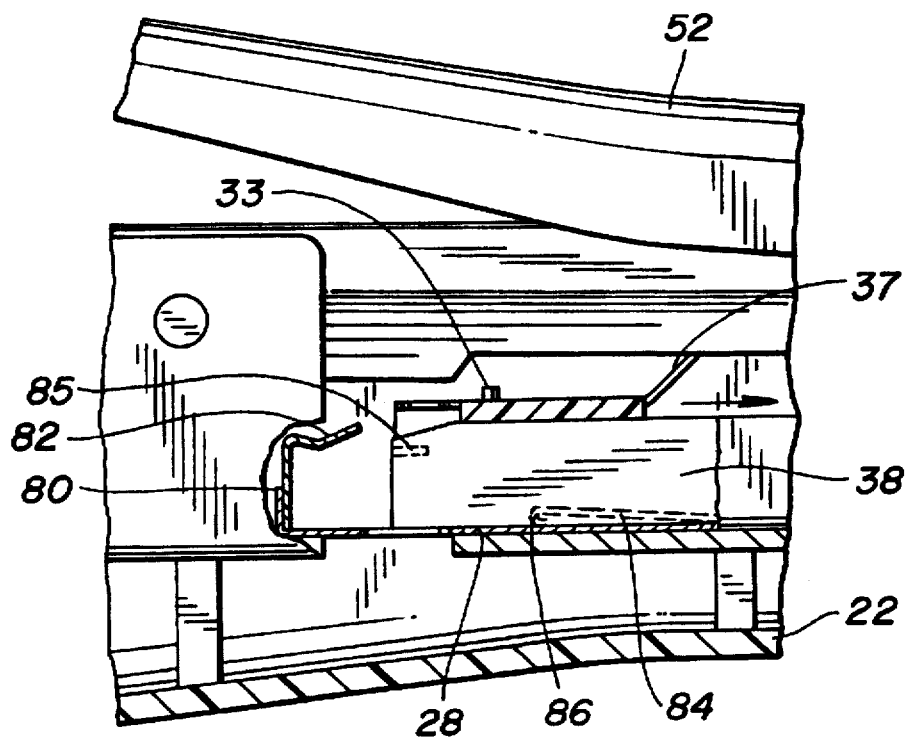
FIG_5

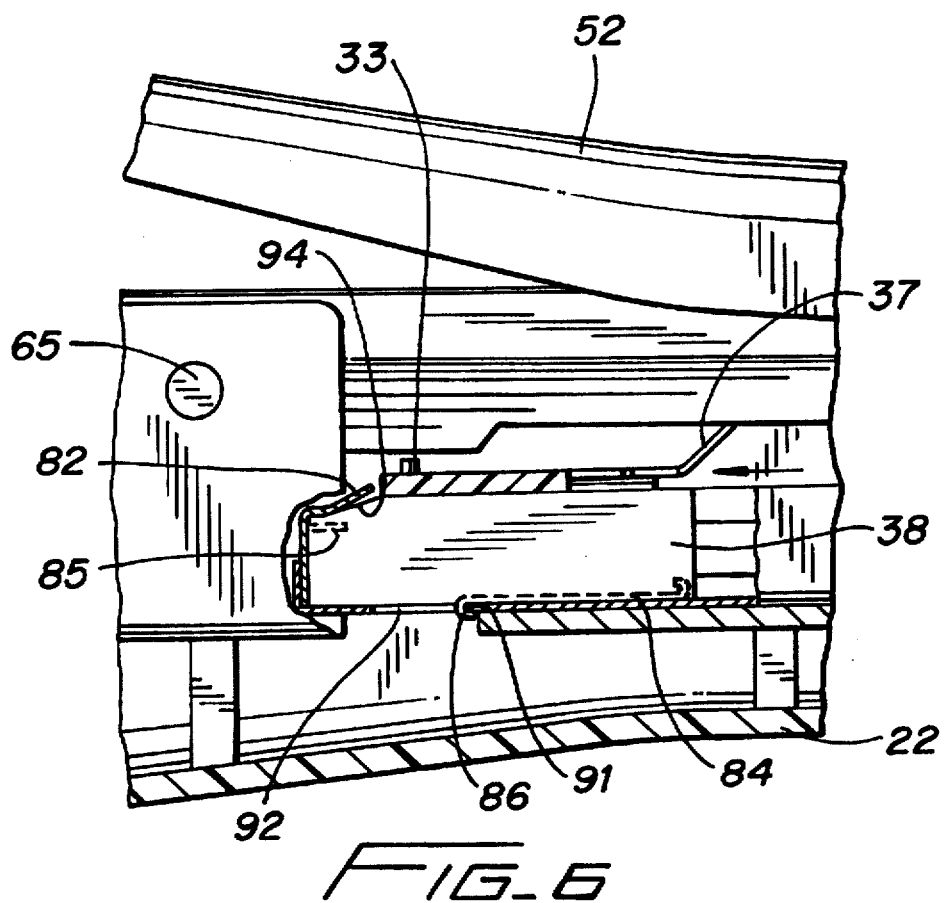
FIG_6

SURGICAL STAPLER WITH LOCKOUT MECHANISM

BACKGROUND

1. Technical Field

This application relates to surgical staplers, and more particularly, to an apparatus for sequentially applying a plurality of surgical fasteners to body tissue and a lockout mechanism therefor.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of staples arranged in at least two lateral rows while the other member comprises an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of such staplers are disclosed in U.S. Pat. Nos. 4,429,695, 5,065,929, and 5,156,614.

Surgical staplers which employ lockout mechanisms to prevent reactuation after firing are also known and are disclosed, for example, in U.S. Pat. Nos. 4,955,959 and 5,031,814. Other staplers having lockout mechanisms are disclosed in U.S. Pat. Nos. Re. 34,519, 5,156,315, and 5,253,793. In such devices, the lockout mechanism prevents the refiring of a spent staple cartridge when the cartridge remains loaded within the surgical apparatus. However, because the mechanism is actuable only after the stapler has been fired, it is ineffective to prevent premature firing of the stapler during shipment.

A surgical stapler employing a shipping interlock is disclosed in U.S. Pat. No. 5,366,133, the disclosure of which is herein incorporated by reference, which prevents premature actuation of the apparatus by jostling and vibrations normally occurring during shipment of the apparatus from the manufacturer to the user and during handling by the user.

The present application provides a shipping interlock and an improved lockout mechanism which prevents reactuation of the stapler.

SUMMARY

The subject application is directed to a surgical stapling apparatus that has one lockout assembly configured to prevent premature actuation of the apparatus during shipment and handling, and another which is configured to prevent refiring of the apparatus. The apparatus includes a cartridge supporting portion having a cartridge positioned therein which contains a plurality of surgical fasteners and a plurality of pushers configured to eject the surgical fasteners from the cartridge. An anvil supporting portion defines an anvil surface against which the surgical fasteners are driven when they are ejected from the cartridge. A cam bar retainer retains at least two cam bars configured to sequentially interact with the pushers as the cam bar retainer translates in a longitudinal (distal) direction from a pre-fired position to a fired position.

The lust lockout assembly includes a pin which extends from the top of the cam bar retainer to interact with a slotted plate provided on the cartridge supporting portion of the stapler. This lockout assembly is disclosed in U.S. Pat. No. 5,366,133 which is incorporated herein by reference.

The second lockout assembly includes a hook-like locking member which is supported on the cam bar retainer and is configured to engage a reception aperture in the cartridge supporting potion when the cam bar retainer is retracted to the post-fired position. A retaining spring member is mounted within the cartridge supporting portion of the stapler and configured to engage a cavity defined in a proximal end of the cam bar retainer when the cam bar retainer is in the pre-fired position. In this position, the retaining spring inhibits proximal movement of the cam bar retainer. The spring moves to a second position during a staple firing operation to allow the cam bar retainer to be withdrawn to the post-fired position.

Further features of the surgical apparatus of the subject application will become more readily apparent to those skilled in the art from the following detailed description of the apparatus taken in conjunction with the drawings.

BRIEF DESCRIPTION OF THE DRAWINGS

Various embodiments of the surgical apparatus of the subject application will be described hereinbelow with reference to the drawings wherein:

FIG. 1 is a perspective view of a surgical stapling apparatus constructed in accordance with a preferred embodiment;

FIG. 2 is a side elevational view of the surgical stapling apparatus of FIG. 1 in partial cross-section illustrating the lockout assembly for preventing refiring in the initial (pre-fired) position;

FIG. 3 is an exploded perspective view of the surgical stapling apparatus illustrated in FIG. 1;

FIG. 3A is an enlarged localized perspective view of the retaining member illustrated in FIG. 2; and FIG. 3B is an enlarged localized perspective view of the hook potion of the lockout assembly illustrated in FIG. 2;

FIG. 4 is an enlarged side elevational view of the lockout assembly illustrated in FIG. 2 with the retaining member engaged in a cavity in the cam bar retainer to maintain the cam bar retainer in a pre-fired position;

FIG. 5 is an enlarged side elevational view of the lockout assembly illustrated in FIG. 2 with the retaining member released from the cavity in the cam bar retainer as the cam bar retainer moves toward a distal position during a staple firing operation; and FIG. 6 is an enlarged side elevational view of the lockout assembly illustrated in FIG. 2 with the retaining member resiliently engaging the cam bar retainer and the hook portion engaging a reception aperture in the carrier channel to maintain the cam bar retainer in a post-fired position.

DETAILED DESCRIPTION OF PREFERRED EMBODIMENTS

In the drawings and in the description which follows, the term "proximal", as is traditional, will refer to the end of the apparatus which is closer to the operator, while the term "distal" will refer to the end of the apparatus which is further from the operator.

Referring now to the drawings wherein like reference numerals identify similar structural elements disclosed herein, there is illustrated in FIG. 1 a surgical stapling apparatus constructed in accordance with a preferred embodiment and designated generally by reference numeral 10. Surgical apparatus 10 is a linear stapling device configured to sequentially apply a plurality of surgical fasteners to body tissue and preferably concomitantly form an incision in the stapled tissue. Although fasteners in the form of staples are shown, it is also contemplated that two piece fasteners, including polymeric fasteners, can be utilized.

Surgical apparatus 10 is provided with a first lockout assembly which prevents premature actuation of the apparatus during shipment and handling, and a second lockout assembly which disables the apparatus after actuation. The specific operation of each lockout assembly is described in greater detail hereinbelow with reference to FIGS. 4–6.

Referring now to FIG. 3, the structural elements of surgical apparatus 10 are illustrated in detail, including the elements which define the two lockout assemblies. Surgical apparatus 10 includes a lower body portion or housing 22 having an elongated cartridge support channel 26 mounted therein. Support channel 26 is dimensioned and configured to receive and detachably support a disposable loading unit, designated generally by reference numeral 25. The disposable loading unit 25 includes an elongated carrier channel 28, a cartridge 30 mounted in a distal portion of carrier channel 28a, a cam bar retainer 38 supporting a pair of elongated cam bars 40a and 40b and a blade carrier 44, and a firing knob 48. Cartridge 30 houses a plurality of surgical fasteners 34 and a plurality of pushers 36 configured to eject the fasteners from the cartridge body when acted upon by an applied driving force. An example of a staple pusher in accordance with the subject application is disclosed in U.S. Pat. No. 4,978,049, the contents of which is incorporated herein by reference.

Cam bars 40a, 40b have angled cam surfaces 42a and 42b, respectively, which interact with pushers 36 as the cam bar retainer 38 is moved relative to carrier channel 28 during a fastener applying operation. This interaction is described in detail in U.S. Pat. No. 4,978,049. Cam bar retainer 38 supports blade carrier 44 between cam bars 40a and 40b, which carries a knife blade 46 configured to form an incision in the body tissue acted upon by surgical apparatus 10. Firing knob 48 is mounted to cam bar retainer 38 to effect movement of cam bar retainer 38 during a fastener applying operation.

With continued reference to FIG. 3, surgical apparatus 10 further includes an upper body portion 52 housing a clamping channel 54 and an elongated anvil support channel 56. The distal portion of channel 56 defines an anvil 55 having a fastener forming surface against which the legs of the surgical fasteners 34 are formed when they are ejected from cartridge 30 (see, for example, U.S. Pat. No. 4,608,981). A pivot pin 58 operatively connects clamping channel 54 and anvil support channel 56, and a leaf spring 60 is provided for biasing the two members with respect to one another. A mounting flange 62 having a reception groove 64 is formed at the proximal end of anvil support channel 56 for detachably engaging a mounting pin 65 disposed at the proximal end of cartridge support channel 26. Alignment struts 68a and 68b depend from anvil support channel 56 for facilitating lateral alignment of anvil support channel 56 and cartridge support channel 26 when the two structures are approximated during assembly.

Clamping channel 54 includes a pair of distally extending clamping legs 70a and 70b which engage a clamp bracket 72 straddling the cartridge support channel 26, and retained within a correspondingly configured retention area 74 defined in lower body portion 22 of surgical apparatus 10. To effect approximation of the anvil support channel 56 and the cartridge support channel 26, i.e. to clamp body tissue therebetween, the upper body portion 52 is urged toward anvil support channel 56 against the bias of leaf spring 60, and the two structures are pivoted about pin 58, such that clamping legs 70a and 70b engage the edge section 72a and 72b of clamp bracket 72. Continued pivotal movement of the upper body portion 52, causes camming interaction between clamping legs 70a and 70b and edge sections 72a and 72b until anvil 55 and cartridge 30 are in substantial parallel alignment with one another. At such a time, surgical apparatus 10 can be actuated to sequentially apply a plurality of surgical fasteners to body tissue and concomitantly form an incision in the stapled tissue.

Referring to FIG. 2, surgical apparatus 10 includes two lockout assemblies. One prevents premature operation of the apparatus during shipment and handling, and the other disables the apparatus after it has been actuated. The shipping lockout assembly is operatively associated with the cam bar retainer 38, and is configured to maintain the earn bar retainer in a pre-fired position (i.e. prevent distal movement) during shipment and handling. It includes a pin 33 which projects upwardly from the top of cam bar retainer 38 to interact with a tapered engagement slot 35 defined in a plate 37 extending from a proximal end of carrier channel 28. This assembly is disclosed in detail in U.S. Pat. No. 5,366,133 and functions to maintain the earn bar retainer in a pre-fired position when pin 33 is engaged in slot 35. Application of sufficient force to ruing knob 48 releases projecting pin 33 from slot 35 as described in the '133 patent.

The second lockout assembly, which is also associated with earn bar retainer 38, is configured to maintain the cam bar retainer in a post-fired position following actuation, i.e. partial or full advancement, so as to effectively disable surgical apparatus 10 until such time as the disposable loading unit 25 is removed from support channel 26 and replaced with a new, fully loaded unit.

Referring to FIG. 3A, the disabling or firing lockout assembly includes a locking member 84 (FIGS. 3 and 3B), preferably formed of spring steel, which has proximal and distal hook portions 86 and 88 formed thereon. Distal hook portion 88 is configured to engage a shelf 90 defined in earn bar retainer 38 so as to become fixedly connected thereto, while the proximal hook portion 86 is configured to engage a reception slot 92 defined in the floor of carder channel 28 (see FIG. 4). Retaining member 80 is preferably formed integral with carrier channel 28 at the proximal end thereof. Retaining member 80 includes a distally extending engaging portion 82 preferably formed of spring-steel and configured to interact with cam bar retainer 38 to inhibit proximal movement of the cam bar retainer in the pre-fired position. Thus, retaining member 80 prevents proximal movement of the cam bar retainer 38 to its post-fired proximal position until the earn bar retainer 38 is advanced distally during actuation.

Referring now in sequential order to FIGS. 4-6, in conjunction with FIG. 2, when surgical apparatus 10 is shipped from the manufacturer, it is provided with a fully loaded disposable loading unit 25 containing a plurality of surgical fasteners 34. During shipment and prior to utilization, earn bar retainer 38, as described above, is maintained against distal movement in its initial pre-fired proximal position illustrated in FIG. 2 due to the interference of projecting pin 33 in the narrow portion of slot 35 of plate 37. Also, as best seen in FIG. 4, the earn bar retainer 38 is secured against proximal movement due to the engagement of the engaging portion 82 of retaining member 80 within correspondingly configured cavity 85 defined in the proximal end of cam bar retainer 38. Thus, during shipment, if the apparatus encounters vibrations or is jostled, the engagement of pin 33 will serve to prevent distal movement of cam bar retainer 38 to prevent premature ejection of surgical fasteners from cartridge body 30 and the engagement of retaining member 80 with cavity 85 will prevent proximal movement of cam bar retainer 38 to prevent premature lockout of the stapler.

In the initial pre-fired position of cam bar retainer 38, the proximal hook portion 86 of locking member 84 is disposed ahead of the distal-most edge of reception slot 92, and is essentially in a non-operative (non-locking) position.

Referring to FIG. 5, during a fastener applying operation, distal movement of firing knob 48 by a user causes cam bar retainer 38 to translate distally, releasing the engaging portion 82 of retaining member 80 from its initial position within cavity 85 and releasing pin 33 from engagement slot 35. At such a time, engaging portion 82 resiliently returns to its normally undeflected (second) position. In this undetected position of engaging portion 82, it will not engage cavity 85 and thus the cam bar retainer 38 can be withdrawn to its proximalmost position described below and shown in FIG. 6. The locking member 84 translates in conjunction with cam bar retainer 38.

When the cam bar retainer 38 has been moved to its distal-most position (not shown) and the fastener applying operation has been completed, the user draws firing knob 48 in a proximal direction, retracting cam bar retainer 38 toward the post-fired locked-out position illustrated in FIG. 6. This post-fired position is proximal of the initial pre-fired position. When cam bar retainer 38 reaches the post-fired position shown in FIG. 6, the engaging portion 82 of retaining member 80 resiliently abuts the outer surface 94 of cam bar retainer 38, and the proximal hook portion 86 of locking member 84 moves into reception slot 92 and engages the distal-most edge 91 thereof, lockingly maintaining cam bar retainer 38 in the post-fired position, and effectively disabling surgical apparatus 10 until such time as the disposable loading unit 25 is removed from support channel 26, and replaced with a new, fully loaded unit That is, until the disposable loading unit is replaced with a loaded unit, the user cannot advance the firing knob 48 and cam bar retainer 38 because hook portion 86 will abut edge 91 of the slot 92.

In an alternate embodiment, engaging portion 82 of retaining member 80 can frictionally engage the cam bar retainer 38 with sufficient force to serve as a shipping interlock. Thus, in such embodiment, the pin 33 and plate 37 can be eliminated, and sufficient force applied to firing knob 48 will release cam bar retainer 38 from the holding force of engaging portion 82.

Although the subject apparatus has been described with respect to preferred embodiments, it will be readily apparent to those having ordinary skill in the art to which it appertains that changes and modifications may be made thereto without departing from the spirit or scope of the appended claims.

What is claimed is:

1. A surgical apparatus comprising:
   a) a cartridge supporting portion having a cartridge disposed therein which contains a plurality of surgical fasteners and a plurality of pushers configured to eject the surgical fasteners from the cartridge;
   b) an anvil supporting portion having an anvil surface against which the surgical fasteners are driven when they are ejected from the cartridge;
   c) a cam bar retainer operatively associated with the cartridge and retaining at least two cam bars configured to sequentially interact with the pushers as the cam bar retainer translates in a distal direction from a pre-fired proximal position;
   d) a retaining member disposed within the cartridge supporting portion and configured in a first position to engage a cavity defined in a proximal end of the cam bar retainer when the cam bar retainer is in the pre-fired proximal position, the retaining member movable to a second position out of engagement with the cavity when the cam bar retainer is advanced from the pre-fired proximal position; and
   e) a locking member supported on the cam bar retainer and configured to engage an aperture provided within the cartridge supporting portion upon retracting the cam bar retainer to a post-fired proximal position.

2. A surgical apparatus as recited in claim 1, further comprising an elongated carrier channel supported within the cartridge supporting portion and housing the cartridge, the cam bar retainer, and the cam bars.

3. A surgical apparatus as recited in claim 2, wherein the locking member extends integrally from a proximal end portion of the carrier channel.

4. A surgical apparatus as recited in claim 1, wherein the pre-fired proximal position is distal of the post-fired proximal position.

5. A surgical apparatus as recited in claim 4, wherein the retaining member engages an outer surface of the cam bar retainer in the second position.

6. A surgical apparatus as recited in claim 2, wherein the aperture is formed in the carrier channel at a proximal end thereof.

7. A surgical apparatus as recited in claim 6, wherein the locking member has a hook portion configured to engage the aperture.

8. A surgical apparatus as recited in claim 3, wherein the retaining member has a distally extending engaging portion.

9. A disposable loading unit for a surgical apparatus comprising:
   a) an elongated carder channel;
   b) a cartridge disposed in a distal portion of the carrier channel and containing a plurality of surgical fasteners and a plurality of pushers configured to eject the surgical fasteners from the cartridge;
   c) a cam bar retainer disposed within the carrier channel and configured to translate therein in a longitudinal direction, the cam bar retainer movable distally from an initial pre-fired proximal position and subsequently retracted to a post-fired proximal most position;
   d) at least two elongated cam bars retained by the cam bar retainer and configured to sequentially interact with the pushers as the cam bar retainer translates in a distal direction;

e) a first member provided at a proximal end of the carrier channel and in contact with the cam bar retainer to maintain the cam bar retainer in the pre-fired position and prevent proximal movement thereof, and f) a second member operatively associated with the cam bar retainer and configured to maintain the cam bar retainer in a post-fired position.

10. A disposable loading unit as recited in claim 9, wherein the first member is formed integral with the carrier channel.

11. A disposable loading unit as recited in claim 10, wherein the cam bar retainer has a cavity defined in a proximal end portion thereof configured to retain the first member when the cam bar retainer is in the pre-fired position.

12. A disposable loading unit as recited in claim 11, wherein the first member is spring biased out of engagement with the cavity and the second member is spring biased to engage an aperture formed in a proximal end of the carrier channel.

13. A disposable loading unit as recited in claim 12, wherein the second member is in the form of a hook and an aperture is formed in the carrier channel adjacent a proximal end thereof for retaining the hook when the cam bar retainer is in the post-fired position.

14. A disposable loading unit as recited in claim 9, wherein the first member is configured to resiliently engage an outer surface of the cam bar retainer when the cam bar retainer is in the post-fired position.

15. A disposable loading unit as recited in claim 9, further comprising a cutting blade retained by the cam bar retainer and configured to translate therewith.

16. A disposable loading unit for a surgical apparatus comprising:
   a) an elongated carrier channel;
   b) a cartridge disposed in a distal portion of the carrier channel and containing a plurality of surgical fasteners and a plurality of pushers configured to eject the surgical fasteners from the cartridge;
   c) a cam bar retainer disposed within the carrier channel and configured to translate therein in a longitudinal direction, the cam bar retainer movable distally from an initial pre-fired proximal position and subsequently retracted to a post-fired proximal most position:
   d) at least two elongated cam bars retained by the cam bar retainer and configured to sequentially interact with the pushers as the cam bar retainer translates in a distal direction;

e) a first member provided at a proximal end of the carrier channel and in contact with the cam bar retainer to maintain the cam bar retainer in the pre-fired position, and f) a second member operatively associated with the cam bar retainer and configured to maintain the cam bar retainer in a post-fired position wherein the pre-fired position is distal of the post-fired position.

17. In a surgical apparatus including a cartridge containing a plurality of surgical fasteners and a plurality of pushers configured to eject the fasteners from the cartridge, an anvil defining a surface against which the surgical fasteners are driven when they are ejected from the cartridge, and a cam bar retainer retaining at least two cam bars configured to sequentially interact with the pushers as the cam bar retainer translates in a distal direction, the improvement comprising:

a lockout assembly including a hook member supported on the cam bar retainer and movable longitudinally therewith, the hook member configured to engage an aperture provided in the surgical apparatus when the cam bar retainer is retracted to a post-fired proximal position so as to prevent distal movement of the cam bar retainer.

18. A surgical apparatus as recited in claim 17, further comprising a retaining member to initially maintain the cam bar retainer in a pre-fired proximal position.

19. A surgical apparatus as recited in claim 18, wherein the retaining member includes a spring biased portion supported and engaged within a cavity defined in a proximal end portion of the cam bar retainer when the cam bar retainer is in the prefired proximal position and disengaged from the cavity when the cam bar retainer is retracted to the post-fired position.

20. A surgical apparatus as recited in claim 19, wherein the lockout assembly further includes an engagement pin projecting from the cam bar retainer and configured to engage a slot defined in a flange supported within the surgical apparatus when the cam bar retainer is in the pre-fired position.

21. A surgical apparatus as recited in claim 20, wherein the aperture which receives the hook member is formed in a cartridge supporting portion which supports the cartridge, the cam bar retainer and the cam bars.

* * * * *